United States Patent
Fayet

(10) Patent No.: US 8,758,362 B2
(45) Date of Patent: Jun. 24, 2014

(54) ASSEMBLY FOR INSERTING A PROBE INTO THE LACRIMAL CANAL BY PUSHING FROM THE SIDE OF THE EYE

(76) Inventor: Bruno Fayet, Paris (FR)

(*) Notice: Subject to any disclaimer, the term of this patent is extended or adjusted under 35 U.S.C. 154(b) by 202 days.

(21) Appl. No.: 13/147,900

(22) PCT Filed: Jan. 11, 2010

(86) PCT No.: PCT/FR2010/000021
§ 371 (c)(1),
(2), (4) Date: Oct. 14, 2011

(87) PCT Pub. No.: WO2010/089472
PCT Pub. Date: Aug. 12, 2010

(65) Prior Publication Data
US 2012/0035614 A1    Feb. 9, 2012

(30) Foreign Application Priority Data
Feb. 4, 2009   (FR) ..................................... 09 00460

(51) Int. Cl.
*A61F 11/00*   (2006.01)
(52) U.S. Cl.
USPC ............................................. 606/108; 604/8
(58) Field of Classification Search
USPC ............ 606/108, 191, 199, 196, 204.45, 107, 606/198, 104; 623/6.12; 604/294, 8, 9
See application file for complete search history.

(56) References Cited

U.S. PATENT DOCUMENTS

| | | | |
|---|---|---|---|
| 4,822,360 A * | 4/1989 | Deacon ....................... | 623/6.13 |
| 6,238,370 B1 | 5/2001 | Neuhann et al. | |
| 7,135,009 B2 * | 11/2006 | Tu et al. ............................ | 604/8 |
| 2002/0151960 A1 * | 10/2002 | Mendius et al. ............. | 623/1.15 |
| 2004/0204704 A1 | 10/2004 | Tamplenizza et al. | |
| 2006/0276738 A1 * | 12/2006 | Becker .............................. | 604/8 |
| 2010/0030126 A1 | 2/2010 | Fayet | |

FOREIGN PATENT DOCUMENTS

EP            1 127 561         8/2001
WO      WO 2007/139919     12/2007

* cited by examiner

*Primary Examiner* — Tuan V Nguyen
*Assistant Examiner* — Tin Nguyen
(74) *Attorney, Agent, or Firm* — Renner, Kenner, Greive, Bobak, Taylor & Weber

(57) ABSTRACT

The invention relates to a monocaniculonasal and/or monocanalicular intubation assembly particularly intended for lacrimonasal imperforation including a probe (1) made of a first material, in particular a flexible material such as silicone, the probe having a substantially cylindrical shape along a longitudinal axis; and a device for inserting the probe into a lacrimal canal or canaliculus. The device includes an insertion tube (10) made of a rigid material, such as a metal, having a distal end opening and a proximal end opening, the tube having a shape and a size enabling it to receive the probe therein; and a mandrel (20) for pushing the probe and expelling the same from the insertion tube by the distal end opening.

6 Claims, 1 Drawing Sheet

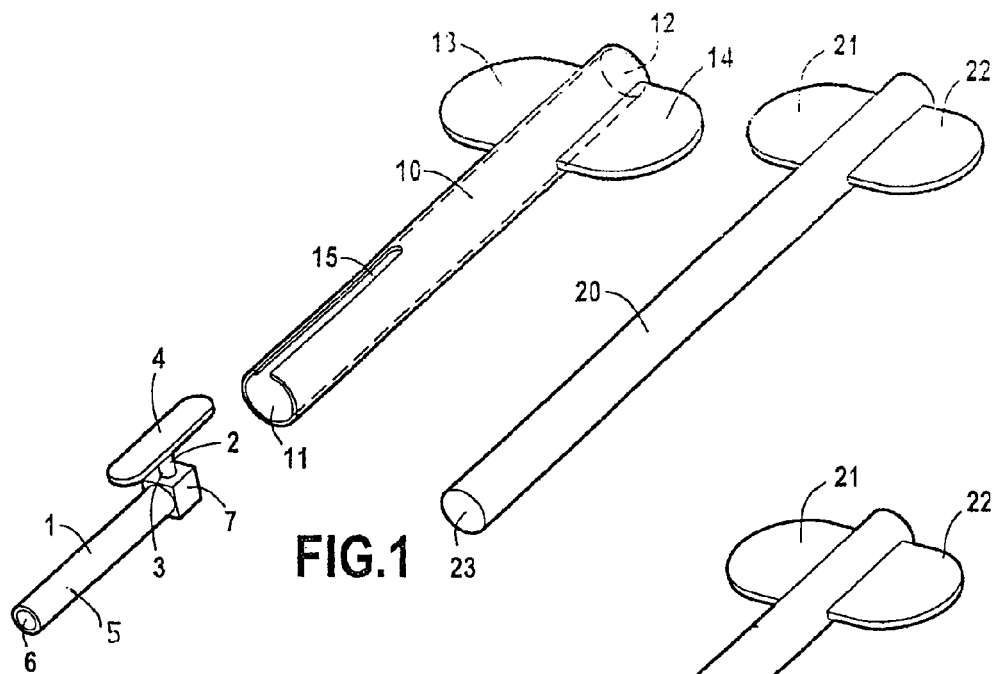
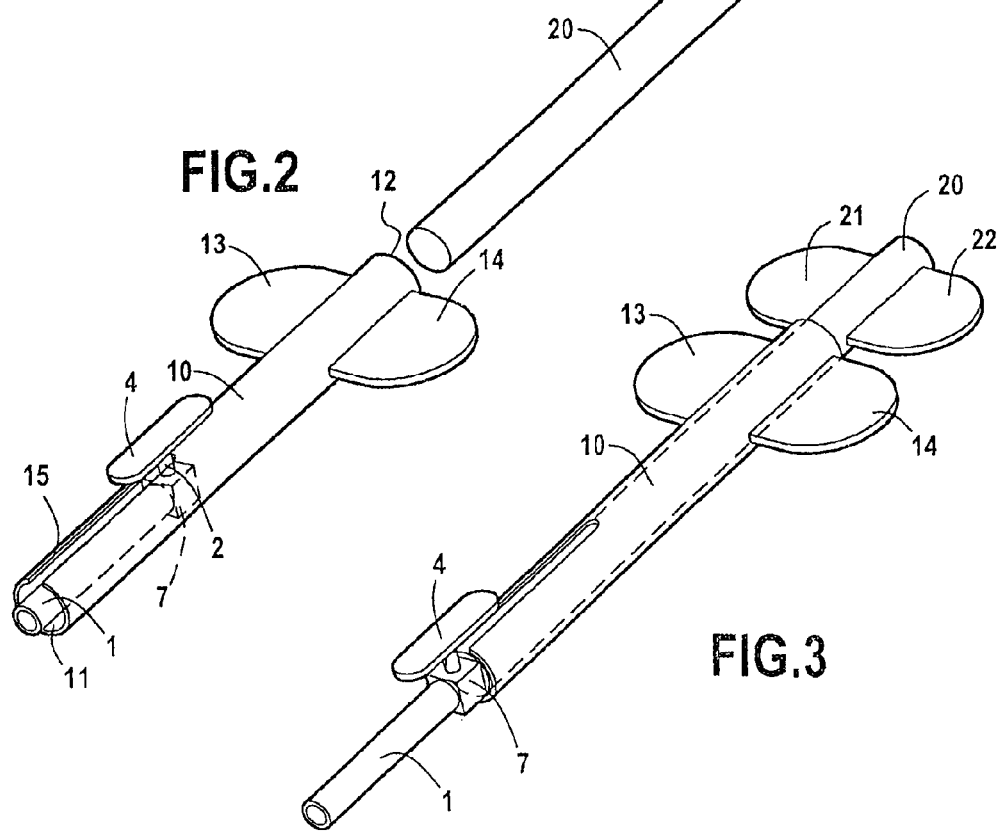

ASSEMBLY FOR INSERTING A PROBE INTO THE LACRIMAL CANAL BY PUSHING FROM THE SIDE OF THE EYE

The present invention relates to a monocaniculonasal and/or monocanalicular intubation assembly intended in particular for lacrimonasal imperforation and canalicular pathologies.

Monocanalicular assemblies are known already in the prior art, in particular through international application WO/2008/056060 in the name of the applicant of the present application, consisting of a metal mandrel and a silicone tube, the mandrel being inserted in the tube to push it from the side of the eye in the lacrimal canal or canaliculus, until it makes contact with the material blocking the canal and passes through said material. With this type of assembly, which allows the tube forming a probe to be inserted from the side of the eye, the need to pass a metal mandrel through the nose, which may prove dangerous, particularly when operating on an infant, is avoided.

However, this type of assembly for insertion by pushing has several drawbacks. Firstly, because of the flexibility of the silicone tube forming a probe, when the mandrel is inserted inside said tube and pushed in the lacrimal canal or canaliculus there is a risk of stretching the side wall of the tube due to friction with the wall of the canal. This stretching then produces spring-back, giving the tube a kinetic energy which may cause it to escape from the lacrimal canal in which it is to be positioned leading to complications for the patient. Secondly, while being pushed the mandrel may perforate the thin wall of the tube, which may also cause complications for the patient. A third drawback is linked to the fact that the mandrel, when being removed from inside the hollow tube forming a probe, may allow germs from the lacrimal passages to pass into the tube, said germs remaining in the tube and possibly proliferating therein, which eventually could also lead to complications. With a process without these drawbacks, a general anaesthetic with assisted mechanical ventilation can be avoided.

The object of the present invention is to overcome the drawbacks of the prior art by proposing a monocanalicular intubation assembly which, while permitting insertion of the probe by pushing from the side of the eye, is also easier for the practitioner to use, with less risk for the patient.

According to the invention, the monocaniculonasal and/or monocanalicular intubation assembly intended in particular for lacrimonasal imperforation comprising:
 a probe made of a first material, in particular a flexible material such as silicone, the probe having a substantially cylindrical form, for example circular cylindrical or elliptical cylindrical, along a longitudinal axis, and
 insertion means for inserting the probe in a lacrimal canal or canaliculus,
is characterised in that the insertion means comprise:
 an insertion tube made of a rigid material such as metal, having a distal end opening and a proximal end opening, the tube having a shape and size enabling it to receive the probe therein; and
 pushing means for pushing the probe and expelling said probe from the insertion tube by the distal end opening.

Thus, with the system according to the invention, it is no longer necessary for the probe to be traversed and penetrated by a metal mandrel, which avoids piercing the wall of the probe. Moreover, when the probe is positioned, the fact that it is protected inside a rigid tube prevents it from being stretched by the inner walls of the canal, which also avoids both any tearing and rotational or translational displacement detrimental to the correct final positioning thereof. Insertion is therefore made easier for the practitioner, who no longer needs to take account of the friction between the lacrimal canal and the silicone probe that he wishes to insert therein, and is less risky for the patient.

According to a preferred embodiment, the pushing means consist of a mandrel made of a second material such as metal, in particular more rigid than the first material, having a shape and size enabling said mandrel to be inserted in the insertion tube by the proximal opening to make contact with the probe inserted in the tube, in particular without penetrating inside same, so that when the tube and the mandrel slide relative to one another, the probe is expelled by the distal outlet opening. According to another embodiment, the pushing means consist of a device having a fluid such as compressed air, said fluid being sent into the insertion tube to expel the probe.

According to a preferred embodiment of the invention, a locking cap deriving the probe, in particular substantially in the region of the proximal portion of the lateral longitudinal surface thereof, is designed to lock the probe in the lacrimal canal. Said locking cap consists of a stem, which has at a free end a flange projecting laterally from said stem, the insertion tube comprising on a distal portion for receiving the cylindrical probe, a longitudinal slit extending in the longitudinal lateral surface of the tube to the distal opening, the width of this slit in the peripheral direction (transversally to the longitudinal axis of the tube) being sufficient to allow the stem of the locking cap to slide along the insertion tube when the tube and the mandrel slide relative to one another, pushing the cylindrical probe and expelling it by the distal opening.

Preferably, the length of the insertion tube is substantially equal to twice the length of the probe.

Preferably, the mandrel has a length substantially equal to that of the insertion tube.

According to an embodiment, the probe is substantially in the form of a hollow tube, of which the transverse internal dimension, in particular the internal diameter, is less than that of the mandrel so that said mandrel cannot penetrate inside the hollow tube.

According to another embodiment, the probe comprises a distal portion in the form of a hollow tube, and a proximal portion in the form of a solid bar, a rear face of which is designed to be pushed by the distal end of the mandrel.

Preferably, the insertion tube, in particular at the proximal end, comprises at least one tab, for example in the form of a half disk, allowing the practitioner to grasp the tube.

Preferably, the mandrel, in particular substantially in the region of its proximal end, comprises at least one tab in the form of a lug for grasping the mandrel to permit a relative displacement of the mandrel in the insertion tube.

According to a preferred embodiment, the probe over at least a portion, in particular the bulb in the region of the proximal end thereof, and the insertion tube are cylindrical with substantially identical non-circular cross-sections, so that the probe cannot twist relative to the insertion tube while it is in said insertion tube, rotation being prevented by the non-circular shapes of the cross-sections of the tube and the probe.

According to a preferred embodiment, the cross-sections of the insertion tube and at least a portion of the probe are elliptical, in particular the bulb of the probe positioned in the region of the proximal end thereof.

The present invention also relates to a monocaniculonasal intubation assembly according to the invention, in which the probe is inserted in the distal end portion of the insertion tube.

According to another preferred embodiment of the invention, the probe is inserted in the insertion tube which comprises a slit, the stem and the flange of a cap derived from the probe projecting outside the slit in the insertion tube.

The present invention also relates to a method of inserting a probe in a canal, for example a lacrimal canal, which consists of taking an insertion tube, in the distal end portion of which the probe has previously been inserted, inserting the mandrel by the proximal opening until it makes contact with a proximal end of the probe, and retracting the insertion tube relative to the mandrel so that the mandrel penetrates even farther into the insertion tube and pushes the probe out of the insertion tube by the distal opening, so that the probe is positioned in the canal, as desired.

An embodiment of the invention will now be described in relation to the accompanying drawings, which are given solely as an example.

FIG. 1 shows the three components of an assembly according to the invention separated from each other;

FIG. 2 shows the three components of FIG. 1 with the probe in the insertion tube before being pushed out of said insertion tube by the mandrel; and FIG. 3 shows the assembly according to the invention while the probe is being expelled from the insertion tube by the mandrel.

FIG. 1 shows the three components of an assembly according to the invention. The first component is a probe 1 in the form of an oblong circular cylinder, having a distal portion 5 in the form of a hollow tube and a proximal portion 7 in the form of a parallelepiped block, also known as the bulb. In the region of the proximal end of the probe 1, in particular in the region of the bulb 7, a locking cap 2 projects consisting of a stem 3 extending along an axis which is substantially transverse, in particular perpendicular, to the longitudinal axis of the cylindrical portion of the probe and a flange 4 projecting laterally from the stem 3. The cylindrical portion 5 of the probe 1 is hollow. However, it is produced so as to give the cylindrical tube great flexibility, in particular if it is made of silicone, and, with a more flexible material, making the cylindrical portion solid may be envisaged.

The second component is a substantially circular and cylindrical tube 10 made of a rigid material, in particular metal, which is open at its distal end 11 and at its proximal end 12. Two tabs 13 and 14 in the form of lugs project from the lateral surface of the rigid insertion tube 10 in the region of the proximal end. On a distal end portion, extending over a length that corresponds substantially to between a half and a third of the total length of the insertion tube, extends a slit 15 which emerges at the distal opening 11 of the insertion tube. The transverse dimension, that is, measured in the peripheral direction of the insertion tube, of the slit 15 is such that the stem 3 of the cap 2 can pass and slide therein when the probe 1 is pushed out of the insertion tube. The internal diameter of the insertion tube, at least in the portion designed to receive the probe, is substantially equal to, while being greater than, the widest transverse dimension of the probe (except for the cap) enabling it to receive the probe (except for the cap) therein.

The third element forming the assembly is a mandrel 20 in the form of a rod made of metal, having a substantially circular cylindrical form, of a size such that said mandrel can be inserted inside the insertion tube by the proximal opening 12 and slide therein. The mandrel 20 comprises at its proximal end two tabs 21, 22 in the form of lugs for grasping by the practitioner. The length of the mandrel is substantially equal to the length of the rigid insertion tube.

FIGS. 2 and 3 show the assembly according to the invention with the silicone probe 1 inserted in the distal end portion of the insertion tube 10. At the same time, the mandrel 20 is inserted by the proximal opening of the insertion tube 10 so that the distal end 23 of the mandrel 20 makes contact with the rear surface of the proximal block 7 of the probe, while the distal end 6 of the probe is located substantially in the region of the distal opening 11 of the insertion tube 10.

The practitioner now inserts the tube from the side of the eye as far as the meatus of the lacrimal canal or canaliculus and then pushes the probe located therein into the lacrimal canal. Accordingly, aided by the tabs 13, 14 and the tabs 21, 22, he pulls the insertion tube towards him while pushing the mandrel stem to prevent said mandrel stem from losing contact with the probe, thus introducing said probe into the lacrimal canal.

This will result in the insertion tube shifting or sliding relative to the probe, the stem 2 sliding along the slit 15 until the probe is completely expelled from the insertion tube into the lacrimal canal.

Once the surgeon has introduced the tube at the end of the lacrimal passages and progressively advanced the probe in the lacrimal passages by pushing until it perforates the obstruction formed in the lacrimal passages so that tears can then flow, the forward movement of the assembly stops when the cap reaches the end of the lacrimal passages and the flange 4 abuts the rim or lacrimal meatus formed at the end of the lacrimal canal.

The final positioning of the probe in the lacrimal canal is thus achieved with the meatal cap positioned in the region of the rim of the meatus. Positioning and placement of the probe is performed easily from the side of the eye without passing through the nose, at the same time ensuring that there is no risk of the mandrel passing through the side wall of the probe tube or of said probe tube becoming detached and escaping from the canal where it is to be inserted due to stretching thereof relative to the mandrel while being positioned, in particular due to friction with the side wall of the lacrimal passages.

According to an enhancement, provision can be made for connecting the insertion tube to the mandrel by an articulation system that can be controlled by pushing, so that the mandrel slides relative to the tube through a control action on said articulation system, for example by a push button, or indeed by electrical or electronic control. For example, a device with a tube and control means may be used, allowing the movement of the mandrel in the tube to be controlled. Screwing the mandrel in the tube and moving it like an endless screw may also be envisaged.

According to an enhancement, at least a portion of the probe, in particular the bulb, has a non-circular cross-section and the insertion tube has a substantially identical, also non-circular, cross-section, their relative sizes being such that the probe is guided by the walls of the tube while being pushed. The non-circularity of the two cross-sections ensures that during guiding the probe is not subject to axial rotation while being pushed in the tube. The cross-sections of the insertion tube and the probe portion, in particular the bulb, may advantageously be elliptical.

The invention claimed is:

1. Monocanaliculonasal and/or monocanalicular intubation assembly intended for lacrimonasal imperforation comprising:

a probe made of a first material and having a distal portion in the form of a hollow tube extending in a longitudinal direction, and a proximal portion in the form of a solid block from which a locking cap projects in a direction transversal to said longitudinal direction, and insertion means for inserting said probe into a lacrimal canal or canaliculus, said insertion means comprising:

an insertion tube made of a second material, said second material being more rigid than said first material, said insertion tube having a distal end opening, and a mandrel for pushing said probe so as to expel it from said distal end opening of said tube, said mandrel having a distal end, wherein said probe and said mandrel are received in said insertion tube, said distal end of said mandrel being in contact with a rear side of said block-shaped proximal portion.

2. The assembly of claim 1, wherein said locking cap comprises a stem which has at a free end a flange projecting laterally from said stem.

3. The assembly of claim 2, wherein said insertion tube comprises a longitudinal slit extending in the longitudinal lateral surface of said tube to said distal opening, the width of said slit being sufficient to allow the stem of the locking cap to slide along the insertion tube.

4. The assembly of claim 1, wherein said block-shaped proximal portion and the insertion tube are cylindrical with substantially identical non-circular cross-sections, so that the probe cannot twist relative to the insertion tube when it is inside said insertion tube, rotation being prevented by the non-circular shapes of the cross-sections.

5. The assembly of claim 1, wherein said insertion tube comprises at least one tab allowing the practitioner to grasp the tube.

6. The assembly of claim 1, wherein said mandrel comprises at least one tab for grasping said mandrel.

* * * * *